United States Patent [19]

Howard, Jr. et al.

[11] Patent Number: 5,209,045
[45] Date of Patent: May 11, 1993

[54] METHOD FOR PREVENTING HEAT LOSS FROM A STERILE IRRIGATION FLUID CONTAINER DURING SURGERY

[75] Inventors: Edward R. Howard, Jr., Dallas, Tex.; Donna L. Klinger, Palmyra, Pa.

[73] Assignee: Techstyles, Inc., Dallas, Tex.

[21] Appl. No.: 871,394

[22] Filed: Apr. 21, 1992

[51] Int. Cl.⁵ .................... B65B 63/08; B65B 55/00
[52] U.S. Cl. ............................. 53/469; 53/440; 604/291; 383/72; 383/113
[58] Field of Search ............... 53/468, 469, 440, 481; 128/750, DIG. 26; 604/37, 187, 291; 383/72, 901, 113

[56] References Cited

U.S. PATENT DOCUMENTS

| | | | |
|---|---|---|---|
| 665,942 | 1/1901 | Tabler | 383/72 |
| 718,053 | 1/1903 | Gregory | 383/72 X |
| 1,276,943 | 8/1918 | Mininberg | 604/291 |
| 1,320,646 | 11/1919 | Paterson | 383/72 X |
| 1,472,032 | 10/1923 | Madaus | 604/291 X |
| 2,949,712 | 8/1960 | Bieberdorf et al. | 53/468 X |
| 3,007,608 | 11/1961 | Cox, Jr. | 53/469 X |
| 3,247,851 | 4/1966 | Seibert | 604/291 |
| 3,695,507 | 10/1972 | Sams | 383/113 X |
| 4,741,909 | 5/1988 | Guthrie | 383/113 X |

Primary Examiner—Horace M. Culver
Attorney, Agent, or Firm—Ross, Howison, Clapp & Korn

[57] ABSTRACT

A sterile bag (10) is provided for containing an irrigation container (20). The bag (10) has an interior (12) for receiving the container (20) and an opening (14). The opening (14) has a tubular member disposed about the opening (14) for receiving a string (16). The string (16) is operable to be tightened to constrict the opening (14) to a size that will receive an irrigation cannula (26).

3 Claims, 1 Drawing Sheet

METHOD FOR PREVENTING HEAT LOSS FROM A STERILE IRRIGATION FLUID CONTAINER DURING SURGERY

TECHNICAL FIELD OF THE INVENTION

The present invention pertains in general to methods for retaining heat in fluid filled containers and, more particularly, to an insulating device for use in association with a sterile irrigation fluid container.

BACKGROUND OF THE INVENTION

During surgery, prewarmed sterile irrigation fluid is contained within a sterile container. This sterile container is typically fabricated from a stainless steel or plastic material, since this material will not present the possibility of breakage and it is also easily sterilized. A predetermined amount of sterile irrigation fluid is disposed at a defined temperature within the container during surgery. A bulb syringe is disposed within the container and this syringe is extracted periodically with a varying amount of fluid contained therein for use in irrigating the body cavity during surgery. However, surgery can typically take anywhere from one to twelve hours and the fluid in these containers typically maintains an acceptable temperature range (33° to 43° C.) for between forty-five minutes to seventy-five minutes. After this time, the fluid must be either rewarmed or replaced to ensure the temperature of fluid is within that acceptable range. At present, no comparable method has been provided for preventing the heat loss in the container in the sterile operating conditions of the operating room. Therefore, there exists a need for an improved method for containing the fluid and preventing heat loss in order to maintain the irrigating fluid at a given temperature for a longer prolonged duration of time. At present, hospitals must discard typically half of their prewarmed sterile irrigating solution due to inadequate temperature.

SUMMARY OF THE INVENTION

The present invention disclosed and claimed herein comprises a method for preventing heat loss from a container of irrigation fluid in an operating room in a sterile environment. The method includes forming a bag of highly heat reflective material and having one open end and one closed end. The container of sterile irrigation fluid is warmed to a predetermined temperature, poured into a graduate container and then inserted into the bag. The open end of the bag has a constricting member that is operable to constrict the opening of the bag down to a substantially closed opening that is sized to allow an irrigation cannula to be disposed therethrough. The irrigation cannula can then extract fluid from the interior of the container and be reciprocated outward and removed for irrigation of the body cavity and then be inserted back in through the constricted opening.

BRIEF DESCRIPTION OF THE DRAWINGS

For a more complete understanding of the present invention and the advantages thereof, reference is now made to the following description taken in conjunction with the accompanying Drawings in which.

DETAILED DESCRIPTION OF THE INVENTION

Figure 1:
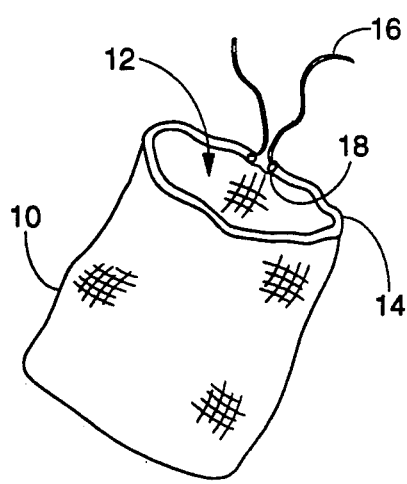
FIG. 1 illustrates a perspective view of the insulated and heat reflective bag of the present invention.

Referring now to FIG. 1, there is illustrated a side view of an insulated bag 10 having an interior cavity 12 with an opening 14 defined at one end. The bag 10 is closed at the opposite end from the opening 14, the opening 14 having a string 16 sewn within a tubular cavity 18 that is disposed around the periphery of the opening 14. The bag 10 is fabricated from a material that has high heat reflective properties, the material fabricated from a metallic-like material such as aluminum. This material is manufactured by Techstyles, Inc. under Part No. 5300-100. The interior cavity 12 is of such dimension that it will allow an irrigation container 20 to be disposed therein.

Figure 2:
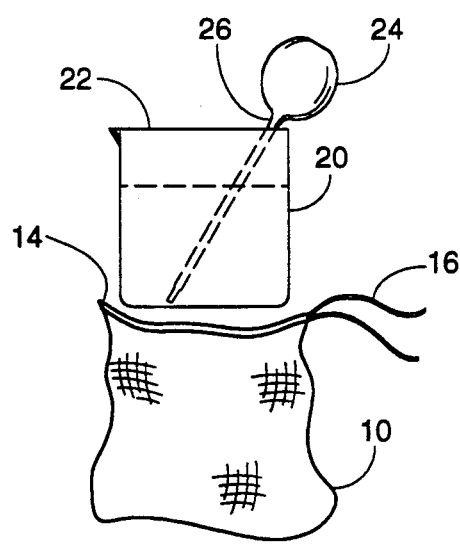
FIG. 2 illustrates a side view of the irrigation container being placed in the insulated bag.

Referring now to FIG. 2, there is illustrated a side view of the irrigation container 20 disposed above and proximate to the opening 14. The irrigation container 20 is fabricated of a stainless steel material and is cylindrical in shape with an open end 22. The open end 22 allows an irrigation fluid to be disposed therein, this fluid represented by a dotted line. A syringe is provided having an applicator bulb 24 attached to a longitudinal cannula 26. The cannula 26 is operable to be disposed within the fluid in the container 20 with the bulb 24 collapsible to provide suction to fill the cannula 26. Therefore, it is imperative that the opening 22 be accessible to the cannula 26.

The opening 22 is configured such that the upper surface of the fluid is exposed to the ambient room temperature, such that evaporation can occur therefrom. Further, the material from which the container 20 is fabricated, i.e., stainless steel, is a very good heat conductor and allows fairly rapid heat transfer across the boundary thereof. As such, the container 20 allows an ideal environment for heat to escape the fluid contained therein.

Figure 3:
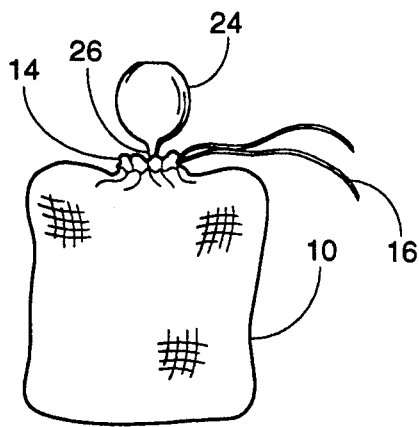
FIG. 3 illustrates a view of the bag closed over the upper portion of the container and enclosing the entire container.
Figure 4:
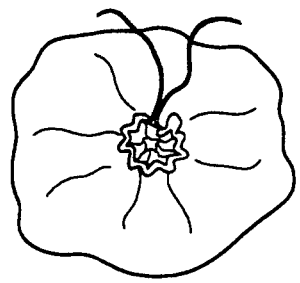
FIG. 4 illustrates a top view of the view of FIG. 3.

As can be seen in FIG. 2, the opening 14 can be expanded to fit over the container 20, with the bag 10 dimensioned on the interior 12 to substantially fit the outer circumference of the container 20. Further, the bag 10 is longer than the container 20, such that the opening 14 can extend past the outer peripheral edges of the opening 22, with the string 16 operable to be pulled together to allow the opening 14 to extend over the opening 22. This is illustrated in FIG. 3. However, it can be seen that the opening 14 is contracted downward to an opening such that cannula 26 is still allowed entrance thereto. This is best seen with respect to the top view of FIG. 4. As such, there now exists a configuration wherein substantially all of the container 20 on the bottom side and peripheral sides thereof is covered in addition to providing a substantial amount of cover over the opening 22. However, there is a small opening that remains for the cannula 26 to protrude therethrough. This allows the operating room nurse to extract the cannula 26 and bulb 24 from the container 20 and reinsert it through the opening 14 after irrigation. Therefore, the procedure is to first sterilize the container 20 and then place sterile irrigation fluid therein. The entire container 20 and fluid contained therein are disposed at the acceptable operating temperature and then inserted into the bag 10. The bag 10 is pulled upward over the outside of the container 20 and then string 16 pulled to contract the opening 14. The opening 14 contracts down to a small opening that is sufficient to allow the cannula 26 to be inserted therethrough. In this configuration, the temperature of the container 20 and the fluid contained therein can be extended. Further, the bag 10 can be designed such that the entire bulb 24 is totally enclosed.

Figure 4A:
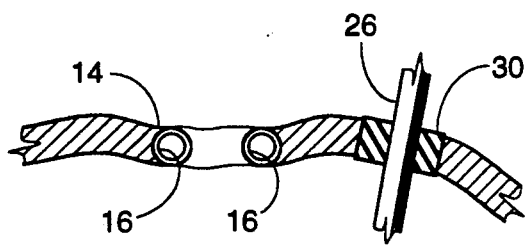
FIG. 4a illustrates an alternate embodiment of the opening in FIG. 4.

In an alternate embodiment illustrated in FIG. 4a, a rubber eyelet 30 is formed within the material of the bag 10 proximate to the peripheral edge of the opening 14. The eyelet 30 is manufactured of a resilient material such as rubber and can be formed integral with the surface of the bag 10. The opening in the eyelet 30 is approximately the size of the cannula 26, if not slightly smaller. However, it should be sized to allow easy insertion of the cannula 26 therein and allow reciprocal movement thereof. Further, a mere opening could also suffice that would be proximate to a part from the opening 14.

Figure 5:
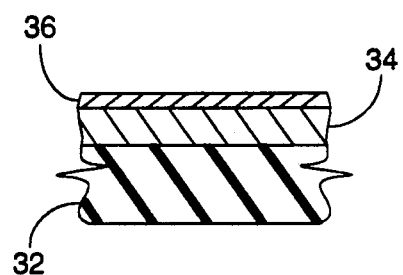
FIG. 5 illustrates a cross-sectional view of the material from which the bag is fabricated.

Referring now to FIG. 5, there is illustrated a cross-sectional diagram of the material from which the bag 10 is frabicated. A layer of polyolefin vinyl 32 is provided on which a layer of aluminum 34 is disclosed. The aluminum layer 34 is approximately 0.001 inches thick and is formed in a conventional manner. An insulating layer 36 is disposed over the aluminum layer 34. In general, the aluminum layer 34 oxidizes upon fabrication, such that the risk of electrical conductivity over the sheet is minimized. This is important in an operating room environment due to the oxygen enriched environment. Further, the layer 36 of insulating material further enhances the noncunductive properties of the overall material. The material illustrated in FIG. 5 is such that it can be sterilized and shipped in a sterile container. This will enhance the overall sterile environment in the operating room. Again, this material is fabricated under Part No. 5300-100 manufactured by Techstyles, Inc.

In summary, there has been provided a method for reducing the heat loss of a container of irrigating fluid in the operating room, while maintaining a sterile environment. A heat reflective bag is provided that is dimensioned slightly larger than the container. The bag is closed at one end with the other end thereof open, the open end being contractible. Once the bag is disposed over the container, the open end is contracted down to a very small opening that will allow a syringe to be disposed therethrough for extracting irrigation fluid therefrom, or the syringe may be totally enclosed for some surgical procedures.

Although the preferred embodiment has been described in detail, it should be understood that various changes, substitutions and alterations can be made therein without departing from the spirit and scope of the invention as defined by the appended claims.

What is claimed is:

1. A method for reducing heat loss in a container of irrigation fluid from which the fluid is retrieved with a longitudinal cannula member with a syringe mechanism disposed on one end thereof, the container cylindrical in shape with one open end and one closed end, comprising the steps of:

providing a bag having one open end and one closed end and peripheral surfaces and dimensions slightly larger than the container, the bag being sterile and having a heat reflective surface;

disposicng the container within the bag after sterilization thereof and insertion of sterile irrigation fluid therein at a predetermined temperature; and contracting the opening of the bag over the opening in the container to a substantially closed opening to substantially reduce the heat loss from the fluid in the container due to evaporation, the substantially closed opening being sized such that the longitudinal cannula member can be inserted therethrough.

2. the method of claim 1 and further comprising providing an orifice in the material in the bag proximate to the opening and sized to allow the longitudinal cannula member to be disposed therethrough and further constricting the opening of the bag such it is substantially closed to allow nothing to be inserted threthrough.

3. The method of claim 1 wherein the material of which the bag is fabricated is comprised of the metallic material providing high reflective heat properties.

* * * * *